United States Patent
Greenfield

[11] Patent Number: 5,891,397
[45] Date of Patent: Apr. 6, 1999

[54] SLIDE ASSEMBLY

[75] Inventor: Walter Greenfield, Scarsdale, N.Y.

[73] Assignee: DiaSys Corporation, Waterbury, Conn.

[21] Appl. No.: 837,843

[22] Filed: Apr. 22, 1997

[51] Int. Cl.⁶ .................................................. B01F 11/00
[52] U.S. Cl. .......................... 422/68.1; 422/72; 422/81;
422/100; 422/102; 73/864.03; 73/864.73;
359/398
[58] Field of Search .................................. 422/68.1, 100,
422/101, 102, 72, 81; 73/864.02, 864.03,
864.73; 359/396, 398

[56] References Cited

U.S. PATENT DOCUMENTS

| 5,248,480 | 9/1993 | Greenfield et al. | 422/68.1 |
|---|---|---|---|
| 5,364,597 | 11/1994 | Polk, Jr. et al. | 422/101 |
| 5,393,494 | 2/1995 | Greenfield et al. | 422/68.1 |
| 5,496,522 | 3/1996 | Vo-Dinh et al. | 422/82.05 |
| 5,503,802 | 4/1996 | Polk, Jr. et al. | 422/101 |
| 5,512,490 | 4/1996 | Walt et al. | 436/171 |

Primary Examiner—Harold Y. Pyon
Attorney, Agent, or Firm—St. Onge Steward Johnston & Reens LLC

[57] ABSTRACT

A glass slide enclosure assembly is described with which fluid couplings can be conveniently made between the enclosure and elongate plastic tubes. Heat shrink conduits are provided and placed around end segments of the glass enclosure and ends of the plastic tubes. The heat shrink tubes are then shrunk by the application of heat. A sealant of light curable type is placed on the end segments of the glass sealant to provide a convenient light activated technique to prevent leakage of body fluid between the heat shrink conduits and the glass enclosure slide.

5 Claims, 2 Drawing Sheets

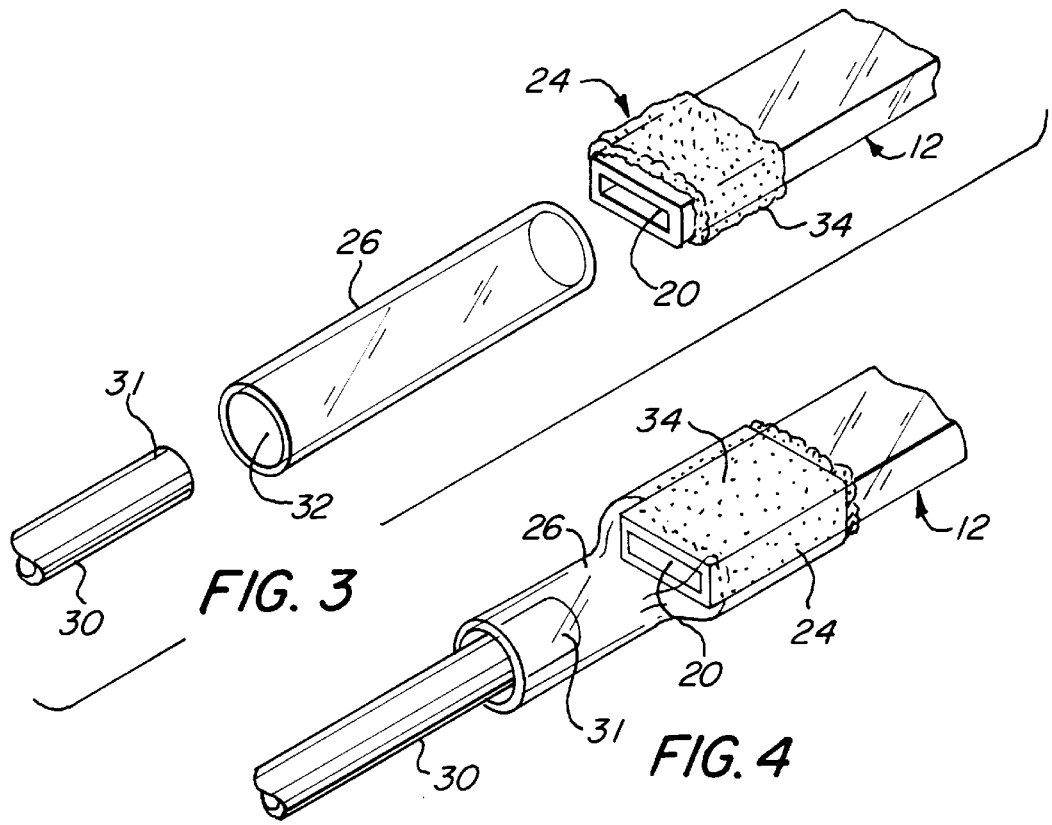
FIG. 3
FIG. 4
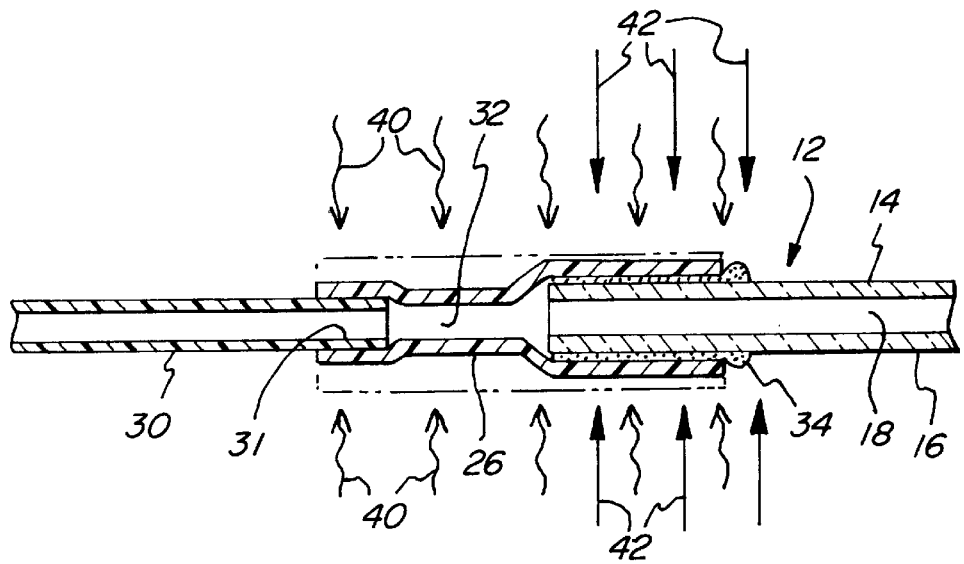
FIG. 5

SLIDE ASSEMBLY

FIELD OF THE INVENTION

This invention generally relates to slide assemblies for use with microscopes and more particularly to glass slide enclosure assemblies which are transparent so that they can be illuminated from one side and microscopically viewed from an opposite side to view a fluid drawn through ports leading to the glass enclosure.

BACKGROUND OF THE INVENTION

In U.S. Pat. No. 5,393,494 an apparatus for drawing a fluid sample through a glass slide assembly is described. That invention involved both an apparatus for moving the fluid and a glass slide assembly through which a fluid sample is drawn for viewing under a microscope. The glass slide assembly consists of an extruded rectangular glass enclosure having parallel walls spaced from each other and having fused connection ports, which provide a transformation from the rectangular cross-section of the glass enclosure to a circular cross-section sized to fit inside the lumen of a plastic tube. Though this slide assembly construction works very well, the addition of fused connection ports involves a complicated process thereby rendering it more difficult to make.

SUMMARY OF THE INVENTION

With a slide assembly in accordance with the invention a rectangular enclosure is extruded from glass and a connection to plastic conduits is made with heat shrink tubes, which are sized to sealingly engage both the glass enclosure and the plastic conduits. An adhesive is employed to provide a firm seal between the glass enclosure and the heat shrink tubes so that no liquid leaks out during use. In a preferred embodiment the adhesive is made of a light activated material so that, after light passing heat shrink tubes are stretched over an end segment of the glass enclosure, the underlying adhesive is cured with light passed through the heat shrink tubes. A similar liquid seal can be employed between the heat shrink tubes and the plastic conduits.

With a slide assembly in accordance with the invention the fusion of glass ports to the rectangular glass enclosure can be avoided and a substantially lower cost glass slide assembly obtained. A glass slide assembly of this invention can be used as a disposable item for a one time use or be reusable for some applications.

It is, therefore, an object of the invention to provide a glass slide assembly, of the viewing chamber type, that is convenient to manufacture and can be made in a cost effective manner. This and other objects and advantages of the invention can be understood from the following detailed description of a preferred embodiment as illustrated in the drawings.

BRIEF DESCRIPTION OF THE DRAWINGS

FIG. 3 is an enlarged exploded perspective view of a step in forming a heat shrink coupling in accordance with the invention;

FIG. 4 is an enlarged view of a heat shrink coupling to a glass viewing chamber during its assembly; and FIG. 5 is a section view of a heat shrink coupling and a forming step thereof in accordance with the invention.

DETAILED DESCRIPTION OF DRAWINGS

Figure 1:
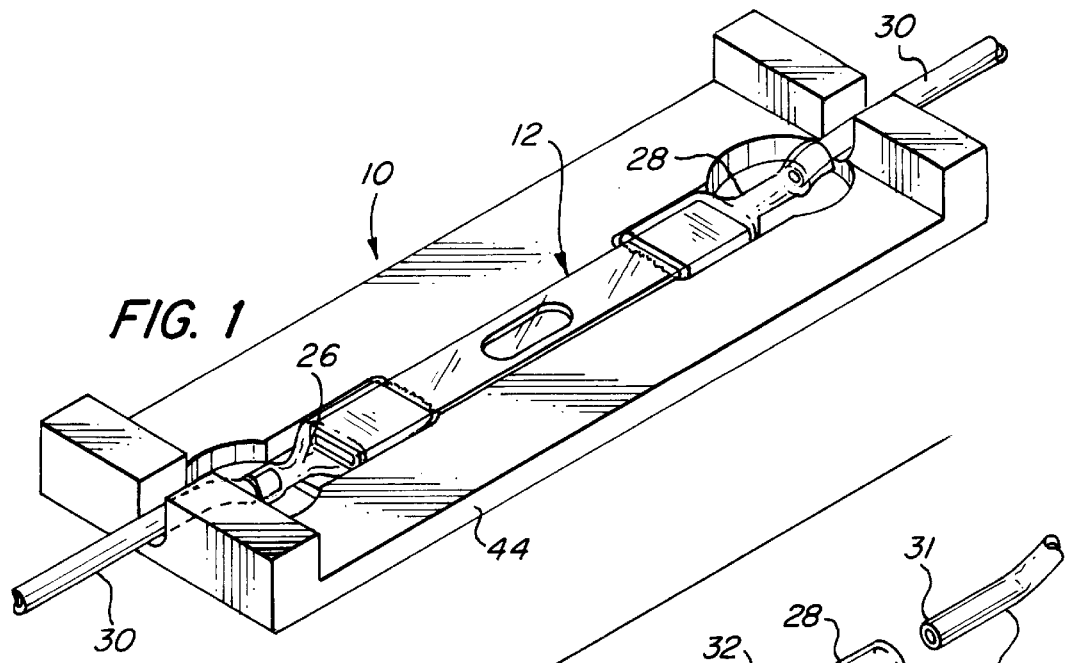
FIG. 1 is a perspective view of a glass slide assembly in accordance with the invention.
Figure 2:
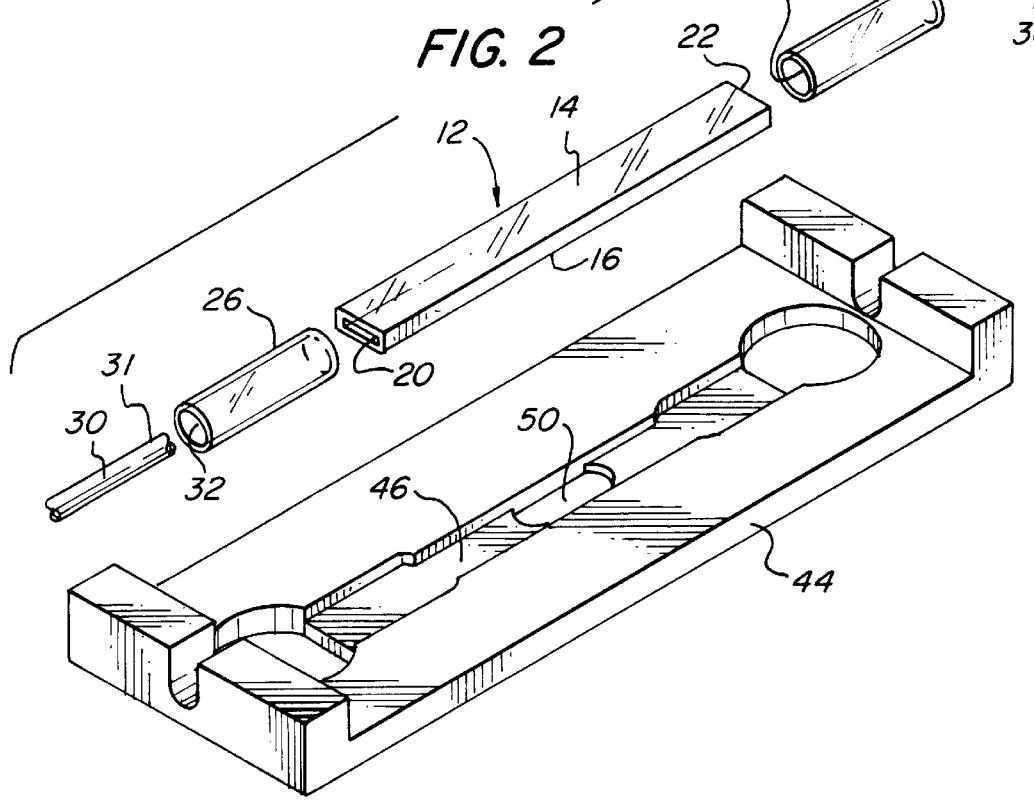
FIG. 2 is an exploded view of the individual parts used to form the glass slide assembly of FIG. 1.

With reference to FIGS. 1 and 2 a glass slide assembly 10 in accordance with the invention is shown. The slide assembly 10 is formed of a glass slide enclosure 12 of the type as illustrated at 320 in FIG. 18 of the aforementioned U.S. Pat. No. 5,393,494. This '494 patent is, therefore, incorporated herein by reference thereto and modified to the extent as described herein.

The glass enclosure 12 has a generally rectangular shape with parallel transparent viewing walls 14, 16 so as to form a viewing chamber 18 into which liquid specimen are drawn in through end located ports 20, 22. The glass enclosure is formed of extruded glass and has end segments 24 with a generally rectangular cross-section. The end segments 24 are coupled by heat shrink conduits 26, 28 to elongate flexible plastic tubes 30. The heat shrink conduits have cylindrical lumens 32, which are sized to fit over the rectangular cross-section of end segments 24. Differently shaped lumens 32 could be used. The plastic tubes 30 freely fit inside the lumens 32 as illustrated in FIG. 4.

The heat shrink conduits 26, 28 are formed of a well known material, which is characterized by an ability to shrink when heated. Such material is well known in the art and available from a number of commercial sources. The heat shrink conduits are preferably though not necessarily formed of a sufficiently transparent plastic material so that they can pass light to fixate a light curable sealant 34 placed between the heat shrink conduits 26, 28 and the glass end segments 24. The light curable sealant can be made of a number of different known materials and preferably is an ultra-violet light cured adhesive. Other types of sealants can be used and they need not be light or UV light curable adhesives.

FIGS. 3–5 illustrate one technique for making a glass slide assembly 12. The end segments 24 of the glass extrusion are coated with the sealant 34 and subsequently the heat shrink conduits 26 are stretched over the end segments 24. Ends 31 of the plastic tubes 30 are then inserted into the lumens 32 and heat applied as illustrated with arrows 40 in FIG. 5. This results in a shrinkage of the conduits 26 and their firm gripping of the end segments 24 and plastic tube ends 31. A fixation of the sealant 34 is then done by exposing the sealant material to ultraviolet light as suggested by arrows 42 in FIG. 5. The sealant 34 serves to both firmly affix the heat shrink conduit to the glass slide and provide an adequate seal to avoid the leakage of body fluids drawn into the viewing chamber formed by the glass slide enclosure 12 during examination under a microscope. If needed a sealant 34 is also used between the plastic tubes 30 and the heat shrink tubes 26, 28. In some cases the sealant need not be made of a light curable material and may even be deleted.

The completed glass slide assembly is then mounted, as shown in FIG. 1, onto a holder 44. The holder 44 has a recess 46 sized to receive the glass slide 12 and a suitable adhesive, not shown, can be used to secure the slide 12 in place on holder 44. An opening 50 in recess 46 serves to enable a back lighting of material drawn into glass slide 12. Note that a holder may not always be needed and that different techniques for holding a glass slide onto a microscope can be used.

Having thus explained an illustrative embodiment of the invention its advantages can be appreciated. Variations from the described embodiment can be made without departing from the scope of the invention as determined by the following claims.

What is claimed is:

1. A slide assembly for use with a microscope, comprising:
    an elongate transparent seamless glass enclosure having elongate upper and lower transparent planar walls which are spaced from each other to form an elongate viewing chamber having a rectangular cross-section for use with a microscope and having rectangularly shaped end segments;
    first and second heat shrink conduits having first and second ends and lumens, with first ends heat shrunk wrapped around the rectangular end segments of the glass enclosure and a sealing material located between the heat shrink conduits and the glass enclosure so as to form a seal therebetween; and
    elongate flexible plastic tubes sized to fit within the lumens of the heat shrink conduits with the second ends of the heat shrink conduits being heat shrunk over, and in sealing relationship with, ends of the plastic tubes.

2. The slide assembly as claimed in claim 1, wherein said first and second heat shrink conduits have an annular shape with their lumens having a cross-sectional size selected so as to be able to fit, prior to heat shrinking, around the rectangularly shaped end segments and the elongate flexible plastic tubes.

3. The slide assembly as claimed in claim 1 wherein said sealing material comprises, a light cured adhesive, and wherein said heat shrink conduits are sufficiently transparent to enable said light cured adhesive to be cured with a beam of light after said heat shrink conduits have been heat wrapped around the rectangular end segments of the glass enclosure.

4. The slide assembly as claimed in claim 3 wherein said sealing material is an ultraviolet cured adhesive.

5. The slide assembly as claimed in claim 1 and further including a slide holder having an elongate recess sized to receive and retain the glass enclosure and an elongate opening inside the recess through which light for a microscopic view of materials inside the glass enclosure can pass.

* * * * *